(12) United States Patent
Wöhl et al.

(10) Patent No.: US 8,492,520 B2
(45) Date of Patent: Jul. 23, 2013

(54) BINDING EPITOPES FOR G250 ANTIBODY

(75) Inventors: Thorsten Wöhl, Planegg (DE); Volker Böttger, Germering (DE)

(73) Assignee: Wilex AG, Munich (DE)

( * ) Notice: Subject to any disclaimer, the term of this patent is extended or adjusted under 35 U.S.C. 154(b) by 330 days.

(21) Appl. No.: 12/740,854

(22) PCT Filed: Oct. 31, 2008

(86) PCT No.: PCT/EP2008/009222
§ 371 (c)(1),
(2), (4) Date: Nov. 8, 2010

(87) PCT Pub. No.: WO2009/056342
PCT Pub. Date: May 7, 2009

(65) Prior Publication Data
US 2011/0123537 A1    May 26, 2011

(30) Foreign Application Priority Data
Nov. 2, 2007 (EP) .................................. 07021425

(51) Int. Cl.
*C07K 7/00* (2006.01)
(52) U.S. Cl.
USPC ..... 530/350; 530/326; 530/387.1; 530/387.7; 435/7.23
(58) Field of Classification Search
None
See application file for complete search history.

(56) References Cited

U.S. PATENT DOCUMENTS

| | | | |
|---|---|---|---|
| 5,955,075 A * | 9/1999 | Zavada et al. | 424/138.1 |
| 6,297,041 B1 * | 10/2001 | Zavada et al. | 435/232 |
| 7,846,673 B2 * | 12/2010 | Pastorek et al. | 435/7.1 |

FOREIGN PATENT DOCUMENTS

| | | |
|---|---|---|
| EP | 0637336 A1 | 8/1995 |
| WO | WO 01/98363 A | 12/2001 |
| WO | WO03/100029 A | 12/2003 |

OTHER PUBLICATIONS

Essen (J. NIH Res. 1995 7:46).*
Spitler (Cancer Biotherapy, 1995, 10:1-3).*
Boon (Adv. Can. Res. 1992 58:177-210).*
Reineke, Ulrich: "Antibody epitope mapping using arrays of synthetic peptides", Methods in Molecular Biology (Clifton, NJ), 2004, vol. 248, 2004, pp. 443-463, XP001539415; ISSN: 1064-3745 p. 452-p. 454.
Uemura, H et al.: "MN/CA IX/G250 as a potential target for immunotherapy of renal cell carcinomas", British Journal of Cancer, Nature Publishing Group, London, GB, vol. 81, No. 4, Oct. 1, 1999, pp. 741-746, XP002300254 ISSN: 0007-0920 p. 742, paragraph 5.
Oosterwijk, E et al.: "Monoclonol Antibody G 250 Recognizes a Determinant Present in Renal-Cell Carcinoma and Absent From Normal Kidney", International Journal of Cancer, John Wiley & Sons, Inc, United States, Switzerland, Germany, vol. 38, Oct. 15, 1986, pp. 489-494, XP008009792 ISSN: 0020-7136.
Pastorek et al: "Cloning and characterization of MN, a human tumor-associated protein with a domain homologous to carbonic anhydrase and a putative helix-loop-helix DNA binding segment", Oncogene, Nature Publishing Group, GB Basingstoke, Hants, vol. 9, No. 10, Oct. 1, 1994, pp. 2877-2888, XP002131890 ISSN: 0950-9232.
International Search Report—PCT/EP2008/009222, (2008).

* cited by examiner

*Primary Examiner* — Sheela J Huff
(74) *Attorney, Agent, or Firm* — Gianna Julian-Arnold; Saul Ewing LLP (57) ABSTRACT

The invention relates to specific amino acid sequences which have been determined to be target epitope for antibodies, in particular, for a G250 antibody.

12 Claims, 3 Drawing Sheets

Fig. 1

Amino acid sequence

Carbonic anhydrase IX:

QRLPRMQEDSPLGGGSSGEDDPLGEEDLPSEEDSPREEDPPGEEDLPGEEDLPE
VKPKSEEEGSLKLEDLPTVEAPGDPQEPQNNAHRDKEGDDQSHWRYGDPPWPRVSPACA
GRFQSPVDIRPQLAAFCPALRPLELLGFQLPPLPELRLRNNGHSVQLTLPPGLEMALGPG
REYRALQLHLHWGAAGRPGSEHTVEGHRFPAEIHVVHLSTAFARVDEALGRPGGLAVLAA
FLEEGPEENSAYEQLLSRLEEIAEEGSETQVPGLDISALLPSDFSRYFQYEGSLTTPPCA
QGVIWTVFNQTVMLSAKQLHTLSDTLWGPGDSRLQLNFRATQPLNGRVIEASFPAGVDSS
PRAAEPVQLNSCLAAGDILALVFGLLFAVTSVAFLVQMRRQHRRGTKGGVSYRPAEVAET
GA

The antibody WX-G250 recognizes sequence LSTAFARV and also ALGPGREYRAL. Both regions form one clearly exposed discontinuous epitope on CA-IX.

SEQUENCE LISTING

<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

```
Leu Ser Thr Ala Phe Ala Arg Val
1               5
```

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

```
Ala Leu Gly Pro Gly Arg Glu Tyr Arg Ala Leu
1               5                   10
```

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

```
Cys Asn Gln Thr Val Cys Leu Ser Thr Ala Phe Ala Arg Val Cys
1               5                   10                  15
```

<210> SEQ ID NO 4
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 4

```
Cys Val Pro Gly Leu Asp Ile Ser Ser Cys Leu Ser Thr Ala Phe Ala
1               5                   10                  15

Arg Val Cys
```

<210> SEQ ID NO 5
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 5

```
Cys Ser Pro Ala Ala Ala Gly Arg Phe Gln Ser Pro Cys Leu Ser Thr
1               5                   10                  15

Ala Phe Ala Arg Val Cys
            20
```

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 6

```
Cys Leu Ser Ala Cys Leu Ser Thr Ala Phe Ala Arg Val Cys
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

```
<400> SEQUENCE: 7

Cys Leu Gly Pro Gly Arg Glu Tyr Arg Ala Leu Cys
1               5                   10

<210> SEQ ID NO 8
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 8

Cys Gly Ser Leu Thr Thr Pro Pro Ala Ala Gln Val Cys Leu Ser Thr
1               5                   10                  15

Ala Phe Ala Arg Val Cys
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 9

Cys Ile Arg Pro Gln Leu Ala Ala Cys Leu Ser Thr Ala Phe Ala Arg
1               5                   10                  15

Val Cys

<210> SEQ ID NO 10
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 10

Cys His Trp Arg Tyr Gly Gly Asp Pro Pro Trp Cys Leu Ser Thr Ala
1               5                   10                  15

Phe Ala Arg Val Cys
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Cys Leu Ser Thr Ala Phe Ala Arg Val Cys Leu Ser Thr Ala Phe Ala
1               5                   10                  15

Arg Val Cys

<210> SEQ ID NO 12
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 12

Cys Ala Leu Leu Pro Ser Asp Phe Ser Arg Cys Leu Ser Thr Ala Phe
1               5                   10                  15
```

```
Ala Arg Val Cys
         20

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 13

Cys Val His Leu Ser Thr Ala Phe Ala Arg Val Cys
1               5                  10

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Ala Leu Gly Pro Gly Arg Glu Tyr Arg Ala Leu Gln Leu His Leu
1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Cys Leu His Thr Leu Cys Leu Ser Thr Ala Phe Ala Arg Val Cys
1               5                  10                  15

<210> SEQ ID NO 16
<211> LENGTH: 18
<212> TYPE: PRT
<213> ORGANISM: Artificial Sequence
<220> FEATURE:
<223> OTHER INFORMATION: Peptide

<400> SEQUENCE: 16

Cys Ala Leu Gly Arg Pro Gly Gly Cys Leu Ser Thr Ala Phe Ala Arg
1               5                  10                  15

Val Cys

<210> SEQ ID NO 17
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 17

Cys Leu Gly Pro Gly Arg Glu Tyr Cys Leu Ser Thr Ala Phe Ala Arg
1               5                  10                  15

Val Cys

<210> SEQ ID NO 18
<211> LENGTH: 422
<212> TYPE: PRT
<213> ORGANISM: Homo sapiens

<400> SEQUENCE: 18
```

```
Gln Arg Leu Pro Arg Met Gln Glu Asp Ser Pro Leu Gly Gly Gly Ser
1               5                   10                  15

Ser Gly Glu Asp Asp Pro Leu Gly Glu Asp Leu Pro Ser Glu Glu
            20                  25                  30

Asp Ser Pro Arg Glu Glu Asp Pro Gly Glu Glu Asp Leu Pro Gly
            35                  40                  45

Glu Glu Asp Leu Pro Gly Glu Glu Asp Leu Pro Glu Val Lys Pro Lys
    50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
                100                 105                 110

Pro Arg Val Ser Pro Ala Cys Ala Gly Arg Phe Gln Ser Pro Val Asp
            115                 120                 125

Ile Arg Pro Gln Leu Ala Ala Phe Cys Pro Ala Leu Arg Pro Leu Glu
    130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
            165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
            195                 200                 205

Phe Pro Ala Glu Ile His Val Val His Leu Ser Thr Ala Phe Ala Arg
            210                 215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
            245                 250                 255

Ser Arg Leu Glu Glu Ile Ala Glu Glu Gly Ser Glu Thr Gln Val Pro
            260                 265                 270

Gly Leu Asp Ile Ser Ala Leu Leu Pro Ser Asp Phe Ser Arg Tyr Phe
            275                 280                 285

Gln Tyr Glu Gly Ser Leu Thr Thr Pro Pro Cys Ala Gln Gly Val Ile
            290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
            325                 330                 335

Asn Phe Arg Ala Thr Gln Pro Leu Asn Gly Arg Val Ile Glu Ala Ser
            340                 345                 350

Phe Pro Ala Gly Val Asp Ser Ser Pro Arg Ala Ala Glu Pro Val Gln
            355                 360                 365

Leu Asn Ser Cys Leu Ala Ala Gly Asp Ile Leu Ala Leu Val Phe Gly
            370                 375                 380

Leu Leu Phe Ala Val Thr Ser Val Ala Phe Leu Val Gln Met Arg Arg
385                 390                 395                 400
```

```
Gln His Arg Arg Gly Thr Lys Gly Gly Val Ser Tyr Arg Pro Ala Glu
            405                 410                 415

Val Ala Glu Thr Gly Ala
            420
```

BINDING EPITOPES FOR G250 ANTIBODY

CROSS-REFERENCE TO RELATED APPLICATIONS

This application is a National Stage Entry and claims the benefit of PCT/EP08/009222 having an International Filing Date of Oct. 31, 2008, and European Application No. 07021425.9 having a filing date of Nov. 2, 2007, the disclosure of each of which is incorporated herein by reference in its respective entirety.

The invention relates to specific amino acid sequences which have been determined to be target epitopes for antibodies, in particular, for a G250 antibody.

The G250 antigen is closely associated with numerous carcinomas such as renal cell carcinoma. The G250 antigen was first described as a kidney cancer-associated antigen (WO 88/08854). Later, it was found to be identical with the tumor-associated antigen MN, a cell surface antigen with carbonic anhydrase activity, also referred to as CA-IX.

Normal CA-IX expression is found in gastric, intestinal and biliary mucosa, where its physiological role resides in pH regulation. Besides its normal expression pattern, CA-IX expression is found in cervical carcinomas, esophageal carcinomas, colorectal carcinomas, lung carcinomas, biliary and clear cell renal cell carcinomas (RCC).

Antibodies against CA-IX, therefore, can be employed for cancer therapy. Anti-G250 antibodies are described, for example, in EP 637 336. Further, WO 02/062972 describes a hybridoma cell line DSM ACC 2526 which produces the monoclonal antibody G250. The monoclonal antibody G250 recognizes an antigen preferably expressed on membranes of renal cell carcinoma cells (RCC), but not expressed in normal proximal tubular epithelium. The G250 antibody binds to the antigen G250, which is also called MN antigen (cf., for example, WO 93/18152) or CA-IX (carbonic anhydrase IX).

The G250 antibody binding site on the CA-IX antigen, however, has not been known so far. This made production, reproducibility and recovery of G250 antibodies difficult, since no specific epitope sequence binding to CA-IX was provided.

Therefore, it was an objective of the present invention to identify the target epitope of the G250 antibody.

According to the invention this problem is solved by providing peptides comprising the amino acid sequence LSTAFARV (SEQ ID NO:1) or the amino acid sequence ALGPGREYRAL (SEQ ID NO:2) or both sequences LSTAFARV (SEQ ID NO:1) and ALGPGREYRAL (SEQ ID NO:2).

The inventors have found that these peptides constitute the target epitope of the G250 antibody, and the G250 antibody, accordingly, binds to said peptides.

The term "G250 antibody", as used herein, refers to antibodies directed against CA-IX antigen and, in particular, to the monoclonal antibody G250 produced by the hybridoma cell line DSM ACC 2526. Since earlier analyses suggested that the CA-IX binding site is a conformational epitope, the peptides of the invention are preferably presented so as to have the conformational structure as in the protein carbonic anhydrase IX. To this end, they are preferably present in sterically constrained form. For example, the peptides can be coupled to a carrier to constrain a particular conformation.

"Carriers", as used herein, means both carrier molecules, to which the peptides can be coupled, as well as articles or surfaces, onto which the peptides can be applied.

Suitable carrier molecules, for example, are 1,3-di(bromomethyl)phenyl, 1,3,5-tri(bromomethyl)-2,4,6-trimethylbenzyl or 1,2,4,5-tetra(bromomethyl) phenyl. By means of such carrier molecules a sterically constrained geometry of the peptides can be obtained.

It is further preferred that the peptide of the invention is a synthetically produced peptide. Also preferably, it is a non-naturally occurring peptide. The sequences of the invention represent the target epitope of CA-IX, so the peptides preferably represent antigens having an antigenic effect. Preferably, the peptides of the invention have a length of at least 8, more preferably at least 10, even more preferably at least 15 and most preferably at least 20 amino acids and up to 300 amino acids, more preferably up to 200 amino acids, in particular, up to 100 amino acids, even more preferably up to 50 amino acids and most preferably up to 30 amino acids. The peptide of the invention is not the complete carbonic anhydrase IX polypeptide.

Especially preferably, the peptides comprise any of the following sequences:

```
                                          (SEQ ID NO: 3)
CNQTVCLSTAFARVC, (SEQ ID NO: 4)
CVPGLDISSCLSTAFARVC, (SEQ ID NO: 5)
CSPAAAGRFQSPCLSTAFARVC, (SEQ ID NO: 6)
CLSACLSTAFARVC, (SEQ ID NO: 7)
CLGPGREYRALC, (SEQ ID NO: 8)
CGSLTTPPAAQVCLSTAFARVC, (SEQ ID NO: 9)
CIRPQLAACLSTAFARVC, (SEQ ID NO: 10)
CHWRYGGDPPWCLSTAFARVC, (SEQ ID NO: 11)
CLSTAFARVCLSTAFARVC, (SEQ ID NO: 12)
CALLPSDFSRCLSTAFARVC, (SEQ ID NO: 13)
CVHLSTAFARVC, (SEQ ID NO: 14)
ALGPGREYRALQLHL, (SEQ ID NO: 15)
CLHTLCLSTAFARVC, (SEQ ID NO: 16)
CALGRPGGCLSTAFARVC, (SEQ ID NO: 17)
CLGPGREYCLSTAFARVC.
```

The invention also encompasses peptides comprising the amino acid sequence LSTAFARV (SEQ ID NO:1) and/or the amino acid sequence ALGPGREYRAL (SEQ ID NO:2), whereby in the indicated sequences one, two or three amino acids are substituted by other amino acids. Sequences like that can be used as antigens of the G250 antibody as well.

Since the peptides of the invention are antigens of the G250 antibody, they can be used to form a vaccine. It is possible thereby to specifically administer the antigenic epitope region, preferably in highly pure form, in order to produce the desired antibody reaction thereby, while at the same time avoiding other reactions, especially other immune reactions, since the complete polypeptide CA-IX need not be administered.

Further, it had been found in the past that purification of the native CA-IX antigen is difficult. This was unfavorable, above all, in respect of the provision of assays.

Therefore, another object of the present invention is an assay for purification of antibodies or binding molecules, comprising (i) providing a peptide of the invention, (ii) contacting a composition comprising antibodies or binding molecules with said peptide, (iii) removing non-binding components, and (iv) recovering the antibodies or binding molecules.

According to the invention an assay is provided, wherein not the native carbonic anhydrase IX peptide is applied but an inventive peptide. In such an assay, the peptide is preferably coupled to a carrier, for example, a carrier of plastics, glass or metal. Since the antigenic epitope is presented in the case of the peptides of the invention, antibodies or binding molecules directed against these epitopes bind with the peptides. Subsequently, non-binding components can be removed and the purified antibodies or binding molecules can then be obtained. The assay for purification according to the invention is especially suitable for purification of G250 antibodies or binding molecules.

The invention further comprises an assay for the detection of antibodies or binding molecules, wherein antibodies or binding molecules directed against the inventive peptide which are present in a sample are detected. To this end, too, a peptide comprising the target epitopes of the invention is provided, and it is not necessary to use native CA-IX antigen. A composition possibly containing antibodies or binding molecules directed against CA-IX is then contacted with the peptide. The peptide is preferably coupled to a carrier in this assay, too. Bindings to the peptide then can be detected by conventional methods, e.g. by direct or indirect labeling. In case antibodies or binding molecules are present, a positive signal is obtained. Preferably, G250 antibodies or binding molecules are detected. An assay of that type is suitable, on the one hand, for the analysis of samples, on the other hand, it may also be used for quality control of G250 antibodies.

The advantage that the inventive peptides can be produced in highly pure form in a simple manner and only the antigenic epitopes can be presented also can be utilized for a screening assay for identification of antibodies or binding molecules for CA-IX, comprising (i) providing a peptide of the invention, (ii) contacting candidate antibodies or binding molecules with said peptide, and (iii) identifying candidate compounds binding to said peptide as G250 antibodies or binding molecules.

Since the invention provides the binding site for G250 antibodies, it is possible to identify other antibodies binding to G250 (and MN or CA-IX, respectively). To this end, candidate antibodies or binding molecules are contacted with the peptides of the invention, and candidate compounds, in the case of which binding is found, can be identified as antibodies or binding molecules for CA-IX. In this way, new G250 antibodies can be provided. The invention, therefore, also relates to binding molecules for the CA-IX antigen which bind to an isolated synthetic peptide comprising the amino acid sequence LSTAFARV (SEQ ID NO:1) and/or ALGPGREYRAL (SEQ ID NO:2). The binding molecules thereby are preferably antibodies. In particular, the binding molecules are not the G250 antibody produced by the hybridoma cell line DSM ACC 2526.

New G250 antibodies can be obtained, for example, by a method for producing or providing an antibody or a binding molecule for CA-IX, comprising (i) providing a peptide of the invention, (ii) generating antibodies or binding molecules which are able to bind to said peptide by testing for the ability of the antibodies or binding molecules to bind to said peptide.

It has been found that several tumors are CA-IX antigen-expressing tumors, e.g. renal clear cell carcinoma, cervical carcinoma, biliary carcinoma, esophagus carcinoma, colorectal carcinoma and lung carcinoma. The now identified epitope sequences LSTAFARV (SEC) ID NO:1) and ALGPGREYRAL (SEQ ID NO:2), therefore, also can be used as markers for the recognition or detection of carcinoma cells, in particular, for the detection of renal clear cell carcinoma cells, cervical carcinoma cells, biliary carcinoma cells, esophagus carcinoma cells, colorectal carcinoma cells or lung carcinoma cells. Detection of said epitope sequences on a cell characterizes the respective cells as carcinoma cells. Thereby, cells having these markers can be recognized as cancer cells. On the other hand, it is possible, for example, to detect cancer cells in vivo in tissue by using specific binding molecules for said markers. Especially preferred is the detection or recognition of renal cell carcinoma cells.

The identification of the antigenic epitopes of the CA-IX antigen, however, does not only enable diagnostic applications but also therapeutic applications. Therefore, the invention also relates to the use of the amino acid sequence LSTAFARV (SEO ID NO:1) and/or of the amino acid sequence ALGPGREYRAL (SEQ ID NO:2) as target. The finding that the sequences given in this invention are specific epitope sequences allows their use as targets, especially as targets in therapy, in particular, for the treatment of cancer. For example, it is possible to specifically and selectively attack cancer cells by means of antibodies directed against the sequences. It is also possible to direct active agents site-specifically to tumor cells by means of combined agents, e.g. a combination of an antibody specific for these sequences and a further anti-cancer agent. For this purpose, the epitope sequence is used as a binding site, either for the therapeutic agent itself or for a targeting aid. Especially preferably, the therapeutic agent itself is an antibody or binding molecule which binds with the target epitopes and, thus, allows to directly affect cancer cells.

The invention, therefore, also relates to the use of an antibody or a binding molecule for therapy, wherein the antibody or binding molecule is able to bind to the amino acid sequence LSTAFARV (SEQ ID NO:1) and/or to the amino acid sequence ALGPGREYRAL (SEQ ID NO:2).

Knowledge of the inventive target sequences allows to use antibodies or binding molecules directed against these sequences directly for therapy.

The invention is further illustrated by the appended Figures as well as the following Examples.

EXAMPLES

Example 1

Identification of Target Peptides

Figure 1:
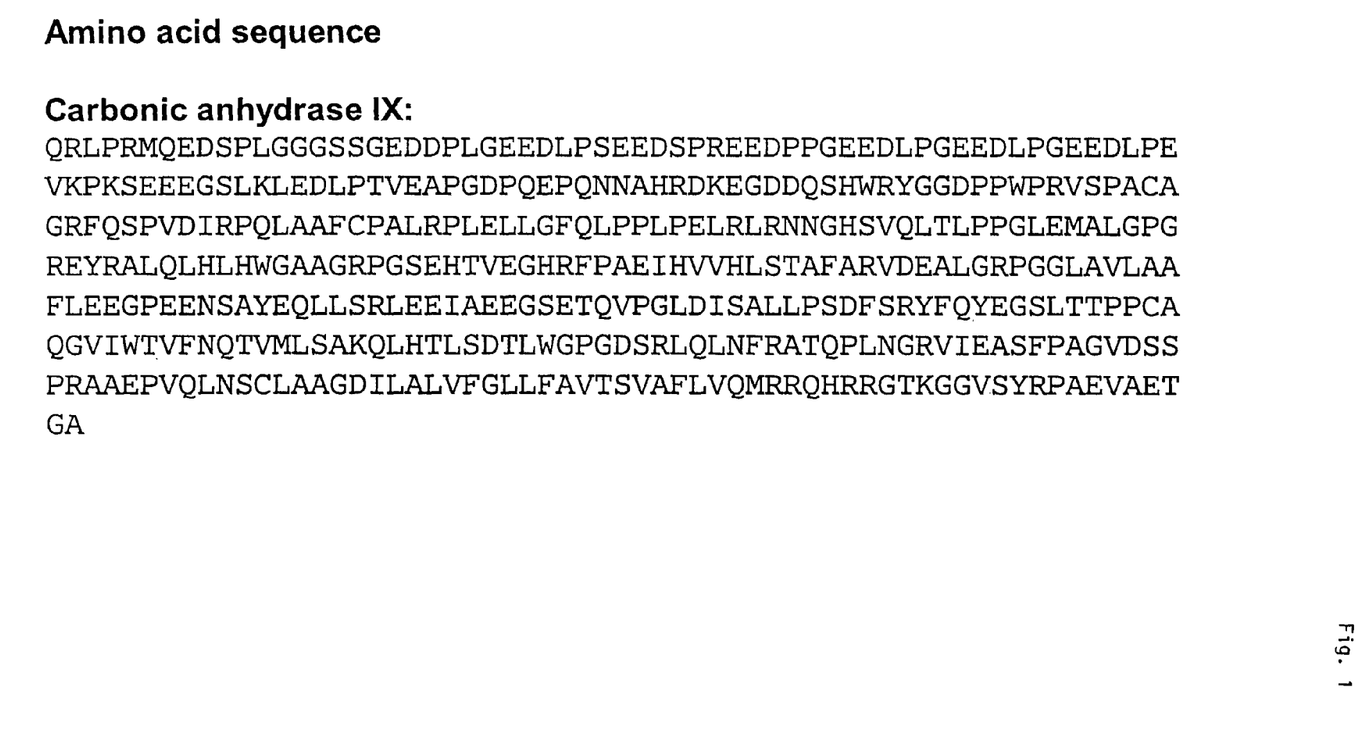
FIG. 1 shows the amino acid sequence of carbonic anhydrase IX.
Figure 2:
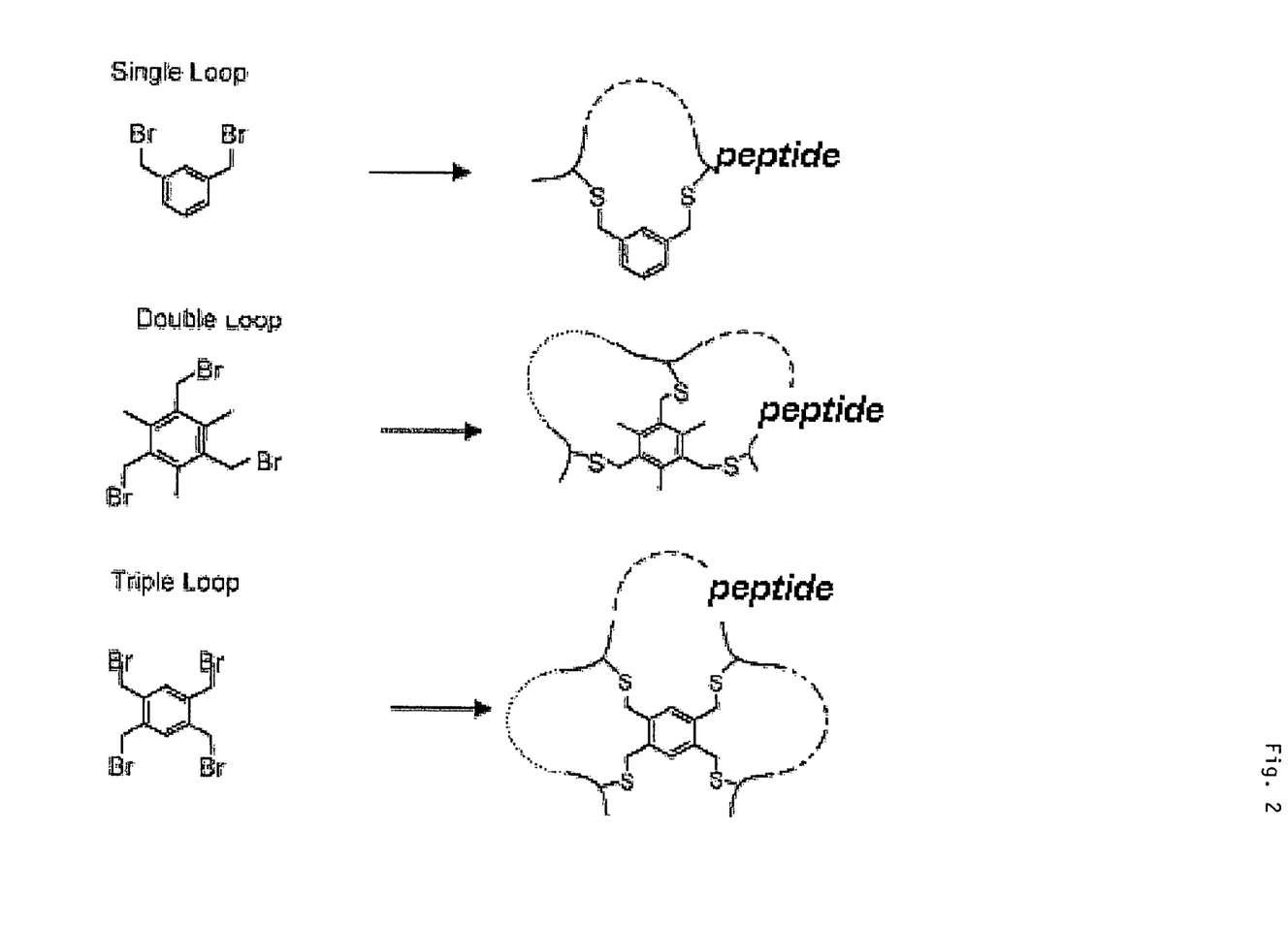
FIG. 2 shows carrier molecules for forming spatially defined peptides to mimic complex protein structures.

Short peptide sections of CA-IX which bind to the G250 antibody were determined by means of conformational epitope mapping of carbonic anhydrase using the scaffolds shown in FIG. 2. The following 15 sequences were identified as peptide sections having the highest binding capacity:

(SEQ ID NO: 3)
CNQTVCLSTAFARVC, (SEQ ID NO: 4)
CVPGLDISSCLSTAFARVC, (SEQ ID NO: 5)
CSPAAAGRFQSPCLSTAFARVC, (SEQ ID NO: 6)
CLSACLSTAFARVC, (SEQ ID NO: 7)
CLGPGREYRALC, (SEQ ID NO: 8)
CGSLTTPPAAQVCLSTAFARVC, (SEQ ID NO: 9)
CIRPQLAACLSTAFARVC, (SEQ ID NO: 10)
CHWRYGGDPPWCLSTAFARVC, (SEQ ID NO: 11)
CLSTAFARVCLSTAFARVC, (SEQ ID NO: 12)
CALLPSDFSRCLSTAFARVC, (SEQ ID NO: 13)
CVHLSTAFARVC, (SEQ ID NO: 14)
ALGPGREYRALQLHL, (SEQ ID NO: 15)
CLHTLCLSTAFARVC, (SEQ ID NO: 16)
CALGRPGGCLSTAFARVC, (SEQ ID NO: 17)
CLGPGREYCLSTAFARVC.

The sequence LSTAFARV (SEQ ID NO:1) is dominantly recognized, followed by the sequence ALGPGREYRAL (SEQ ID NO:2).

Example 2

Localization of Identified Epitope on CA-IX

Figure 3:
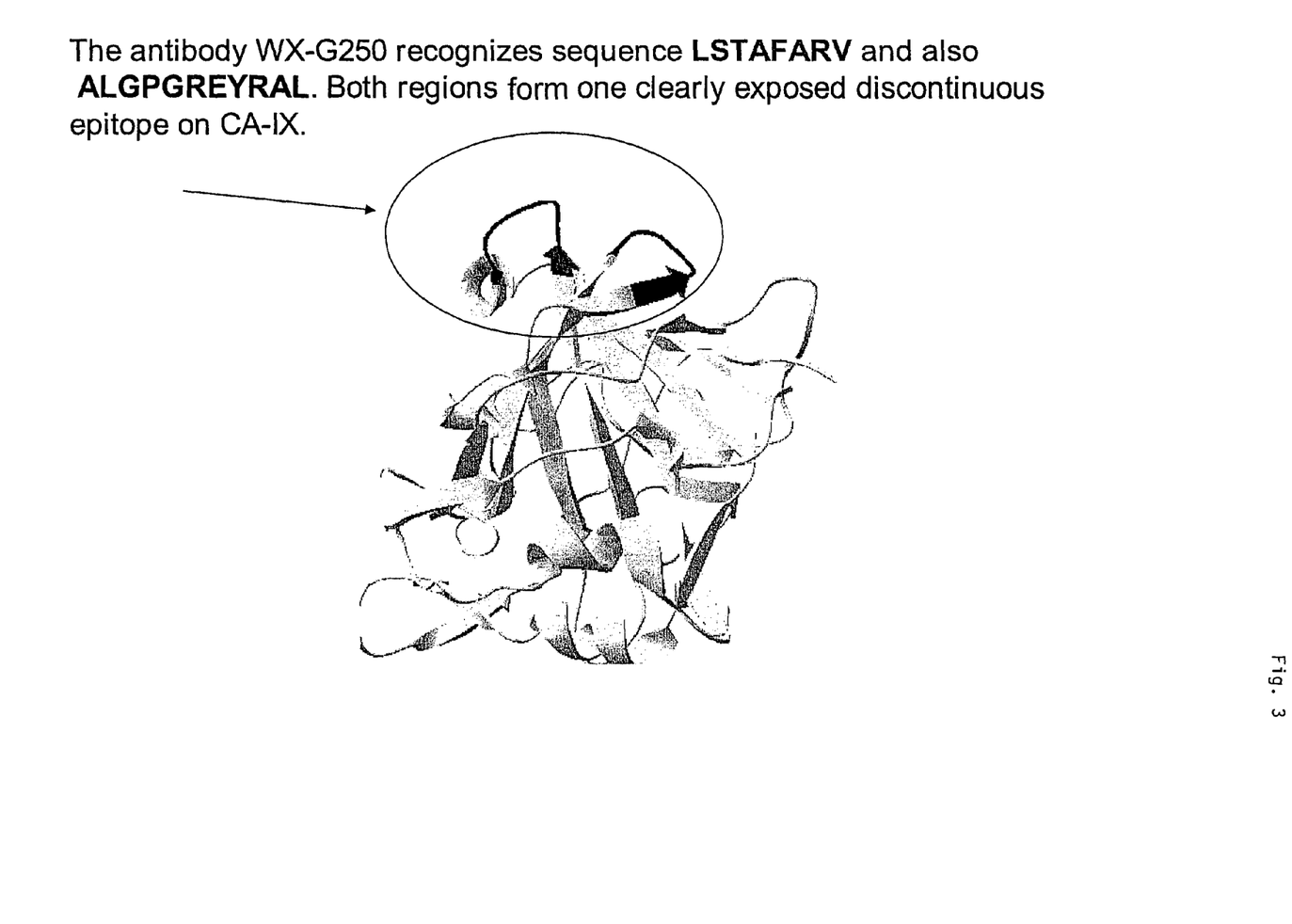
FIG. 3 shows the localization of the epitope sequences LSTAFARV (SEQ ID NO:1) and ALGPGREYRAL (SEQ ID NO:2) according to the invention. Both regions form a clearly exposed discontinuous epitope on CA-IX.

The localization of the identified target sequence sections was shown on a three-dimensional model of CA-IX (cf. FIG. 3).

Example 3

Characterization of G250 Antibody Binding Site

The CA-IX protein is composed of a large extracellular domain (ECD), a single-path transmembrane region (TM) and a short intracellular tail (IC). ECD consists of an N-terminal proteoglycan-like region (PG) and a well-conserved, catalytically active carbonic anhydrase (CA) domain. For better understanding of G250 antibody properties, the location of its binding site was analyzed.

For this, MDCK canine kidney cells permanently transfected with the full-length CA-IX cDNA in pSG5C plasmid (MDCK-MN) or with plasmidS derived therefrom encoding a dCA variant (MDCK-dCA), a dPG variant (MDCK-dPG) or hAS (human alternatively spliced protein truncated in the C-terminal part of the CA domain, MDCK-hAS). Mock transfected cells (MDCK-neo) were used as a negative control. A dCA variant means a CA domain deleted variant.

The binding of G250 antibody to the various cells was tested by incubating microplate wells which were coated with the respective cells each with G250 antibody. Peroxidase-labeled pig anti-mouse IgG was used as detector.

The obtained results showed that G250 antibody binds to a conformational epitope localized in the CA domain of CA-IX.

---

The invention claimed is:

1. A peptide comprising the amino acid sequence LSTAFARV (SEQ ID NO:1) and the amino acid sequence ALGPGREYRAL (SEQ ID NO:2), wherein the peptide is not carbonic anhydrase IX, LSTAFARV (SEQ ID NO:1) and ALGPGREYRAL (SEQ ID NO:2) constitute target epitopes of the G250 antibody, and the peptide has a length of up to 200 amino acids.

2. The peptide of claim 1, wherein the peptide is a synthetic peptide.

3. The peptide of claim 1, wherein the peptide is sterically constrained.

4. The peptide of claim 1, wherein the peptide is an antigen.

5. The peptide of claim 1, wherein the peptide is coupled to a carrier.

6. A method for purifying antibodies or binding molecules directed against the tumor-associated antigen MN or carbonic anhydrase IX, comprising:
   providing a peptide according to claim 1,
   contacting a composition comprising antibodies or binding molecules directed against the tumor-associated antigen MN or carbonic anhydrase IX with said peptide,
   removing non-binding components, and
   recovering the antibodies or binding molecules.

7. The method of claim 6, wherein said peptide is coupled to a carrier molecule selected from the group consisting of 1,3-di(bromomethyl)phenyl, 1,3,5-tri(bromomethyl)-2,4,6-trimethylbenzyl, and 1,2,4,5-tetra(bromomethyl)phenyl.

8. A method for the detection of antibodies or binding molecules directed against the tumor-associated antigen MN or carbonic anhydrase IX, comprising:
   providing a peptide according to claim 1, wherein said peptide is directly or indirectly labeled with a molecule capable of providing a detectable signal,
   contacting a composition suspected to contain antibodies or binding molecules directed against the tumor-associated antigen MN or carbonic anhydrase IX with said peptide, and detecting components of the composition binding to said peptide by detecting the signal provided by the labeling molecule.

9. The method of claim 8, wherein said peptide is coupled to a carrier molecule selected from the group consisting of 1,3-di(bromomethyl)phenyl, 1,3,5-tri(bromomethyl)-2,4,6-trimethylbenzyl, and 1,2,4,5-tetra(bromomethyl)phenyl.

10. A method for detecting the presence of carcinoma cells, comprising:
    providing an antibody directed against the peptide according to claim 1, wherein the amino acid sequence LSTAFARV (SEQ ID NO:1) of said peptide and the amino acid sequence ALGPGREYRAL (SEQ ID NO:2) of said peptide are markers for the recognition and detection of the carcinoma cells,
    contacting a sample suspected to contain said carcinoma cells with said antibody directed against said peptide, and
    detecting said carcinoma cells by detecting the specific binding of said peptide to said carcinoma cells.

11. The method of claim 10, wherein said carcinoma cells are selected from the group consisting of renal clear cell carcinoma, cervical carcinoma, biliary carcinoma, esophagus carcinoma, colorectal carcinoma, and lung carcinoma.

12. A method for producing an antibody or a binding molecule against the tumor-associated antigen MN or carbonic anhydrase IX, comprising:
    providing a peptide according to claim 1, and
    using said peptide as an immunizing antigen.

* * * * *